(12) United States Patent
Fagin et al.

(10) Patent No.: US 8,083,685 B2
(45) Date of Patent: Dec. 27, 2011

(54) SYSTEM AND METHOD FOR LAPAROSCOPIC NERVE DETECTION

(75) Inventors: Randy Fagin, Austin, TX (US); Jon Schiff, Austin, TX (US); Jann Bonfils, Cedar Park, TX (US)

(73) Assignee: ProPep, LLC, Austin, TX (US)

( * ) Notice: Subject to any disclaimer, the term of this patent is extended or adjusted under 35 U.S.C. 154(b) by 952 days.

(21) Appl. No.: 11/745,505

(22) Filed: May 8, 2007

(65) Prior Publication Data

US 2008/0281313 A1 Nov. 13, 2008

(51) Int. Cl.
*A61B 5/05* (2006.01)

(52) U.S. Cl. .................................................. 600/554

(58) Field of Classification Search ............... 600/554, 600/547, 427, 545, 301, 587
See application file for complete search history.

(56) References Cited

U.S. PATENT DOCUMENTS

| | | | |
|---|---|---|---|
| 5,284,154 A * | 2/1994 | Raymond et al. | 600/554 |
| 5,560,372 A | 10/1996 | Cory | 128/741 |
| 5,775,331 A * | 7/1998 | Raymond et al. | 600/554 |
| 6,609,018 B2 | 8/2003 | Cory et al. | 600/393 |
| 6,810,281 B2 * | 10/2004 | Brock et al. | 600/427 |
| 2006/0015162 A1* | 1/2006 | Edward et al. | 607/105 |
| 2007/0021803 A1* | 1/2007 | Deem et al. | 607/46 |

OTHER PUBLICATIONS

Akagami, Ryojo, Charles C.J. Dong, and Brian D. Westerberg "Localized Transcranial Electrical Motor Evoked Potentials for Monitoring Cranial Nerves in Cranial Base Surgery" *Operative Neurosurgery 1*, vol. 57, Jul. 2005 (pp. 78-85).

Brown, William F. and James Veitch "AAEM Minimonograph #42: Intraoperative Monitoring of Peripheral and Cranial Nerves" *Muscle and Nerve*, Apr. 1994 (pp. 371-377).

Calancie, Bill and Nathan Lebwhol "Stimulus-Evoked EMG Monitoring During Transpedicular Lumbosacral Spine Instrumentation, Initial Clinical Results" *Spine*, vol. 19, No. 24, Apr. 6, 1994 (pp. 2780-2786).

Chang, David T., Erik t. Golubuff, and Carl A. Ollson "Use of a New Nerve Stimulator During Radical Prostatectomy" *Blue Torch Medical Technologies, Inc.*, http://www.bluetorchmed.com/surgeons/surg_surgical_techniques.htm, 1998 (7 pages).

Cheung, Albert T., Alberto Pochettino, Michael L. McGarvey, Jehangir J. Appoo, Ronald M. Fairman, Jeffrey P. Carpenter, William G. Moser, Edward Y. Woo, and Joseph E. Bavaria "Strategies to Manage Paraplegia Risk After Endovascular Stent Repair of Descending Thoracic Aortic Aneurysms" *ScienceDirect—The Annals of Thoracic Surgery*, Apr. 21, 2005 (2 pages).

Deletis, Vedran and David B. Vodusek "Intraoperative Recording of the Bulbocavernosus Reflex [Clinical Studies]" (*Ovid*) *Neurosurgery Online*, vol. 40(1), http:/gateway.ut.ovid.com.ezproxy.hsclib.sunysb.edu/gwl/ovidweb.cgi, Jan. 1997 (pp. 88-93).

(Continued)

*Primary Examiner* — Max Hindenburg
*Assistant Examiner* — Fangemonique Smith
(74) *Attorney, Agent, or Firm* — Rebecca J. Brandau (57) ABSTRACT

A surgical system aids identification of nerves in a body to help prevent damage to the nerves during surgery to the body proximate the nerves. An electrode introduced to within a body cavity through a catheter is placed proximate a nerve within the body cavity by a laparoscopic or robotic device. An exploratory probe placed in the body cavity is selectively placed along a presumed pathway of the nerve to provide an electrical signal through the nerve to the electrode. An analyzer interfaced with the electrode analyzes the electrical signal received at the electrode to determine the proximity of the exploratory probe to the nerve, allowing mapping of the nerve pathway through the body cavity.

21 Claims, 5 Drawing Sheets

OTHER PUBLICATIONS

Dong, Charles C.J., David B. MacDonald, Ryojo Akagami, Brian Westerberg, Ahmed AlKhani, Imad Kanaan, and Maher Hassounah "Intraoperative Facial Motor Evoked Potential Monitoring with Transcranial Electrical Stimulation During Skull Base Surgery" *Clinical Neurophysiology* 116 2005, *International Federation of Clinical Neurophysiology, Elsevier Ireland, Ltd*. Sep. 13, 2004 (pp. 588-596).

Freedman, Brett A. and Benjamin K. Potter, Timothy R. Kuklo "Managing Neurologic Complications in Cervical Spine Surgery" *Current Opinion in Orthopaedics*, vol. 16, 2005 (pp. 169-177).

Gartsman, Gary M. And Samer S. Hasan "Specialty Update: What's New in Shoulder and Elbow Surgery" *The Journal of Bone and Joint Surgery, Incorporated*, vol. 88-A, No. 1, Jan. 2006 (pp. 230-243).

Herdmann, Jörg, Klaus Bielefeldt, and Paul Enck "Quantification of Motor Pathways to the Pelvic Floor in Humans" *The American Physiological Society*, Dec. 6, 1990 (pp. G720-G-723).

Isley, Michael R., Michael J. Cohen, James S. Wadsworth, Samuel P. Martin, Jr., and Mary Ann O'Callaghan "Multimodality Neuromonitoring for Cartid Endarterectomy Surgery: Determination of Critical Cerebral Ischemic Thresholds" *American Journal of Electroneurodiagnostic Technology*, vol. 38, No. 2, Jun. 1998 (pp. 1-27).

Kartush, Jack M., Malcolm A. Graham, and Kenneth R. Bouchard "Intraoperative Facial Nerve Monitoring at Michigan Ear Institute" www.michiganear.com/library/F/facemon.pdf, Feb. 20, 1998 (10 pages).

Krassioukov, Andre, Roger Sarjeantm Homan Arkia, and Michael G. Fehlings "Multimodality Intraoperative Monitoring During Complex Lumbosacral Procedures: indications, techniques, and long-term follow-up review of 61 consecutive cases" *J. Neurosurg: Spine*, vol. 1, Oct. 2004 (pp. 243-253).

Kurstjens, G.A.M., A. Borau, A. Rodriguez, N.J.M. Rijkoff and T. Sinkjaer "Intraoperative Recording of Electroneurographic Signals From Cuff Electrodes on Extradural Sacral Roots in Spinal Cord Injured Patients" *The Journal of Urology*, vol. 174, Oct. 2005 (pp. 1482-1487).

Lopéz, Jamie R., Steve D. Chang, and Gary K. Steinberg "The Use of Electrophysiological Monitoring in the Intraoperative Management of Intracranial Aneurysms" Jul. 13, 1998, *J. Neurol. Neurosurg. Psychiatry* vol. 66, 1999 (pp. 189-196).

Matz, Paul G., Charles Cobbs and Michael S. Berger "Intraoperative Cortical Mapping as a Guide to the Surgical Resection of Gliomas" *Journal of Neuro-Oncology*, vol. 42, 1999 (pp. 233-245).

Møoller, Aage R. "Monitoring Techniques in Cavernous Sinus Surgery" Chapter 15, Part III, Monitoring of Brain and Cranial Nerve Function *Intraoperative Neurophysiologic Monitoring in Neurosurgery* Sep. 1991 (pp. 141-153).

Pearlman, Ronald, Michael R. Isley, Garry D. Ruben, Steven C. Sandler, Bertram Weisbaum, Mohammad Ali Khan, Barry S. Green, Vijayan Charles, and Ajot Shah "Intraoperative Monitoring of the Recurrent Laryngeal Nerve Using Acoustic, Free-Run, and Evoked Electromyography" *Journal of Clinical Neurophysiology*, vol. 22, No. 2, Apr. 2005 (pp. 148-152).

Schmalzried, Thomas P., Harlan C. Amstutz, and Frederick J. Dorey "Nerve Plasy Associated with Total Hip Replacement" *The Journal of Bone and Joint Surgery*, vol 73-A, No. 7, Aug. 1991 (pp. 1074-1080).

Schmid, Daniel M., A. Curt, D. Hauri, and B. Schurch "Motor Evoked Potentials (MEP) and Evoked Pressure Curves (EPC) From the Urethral Compressive Musculature (UCM) by Functional Magnetic Stimulation in Healthy Volunteers and Patients with Neurogenic Incontinence" *Neurology and Urodynamics*, vol. 24, 2005 (pp. 117-124).

Smith, Judith W., Paul M. Pellicci, Nigel Sharrock, Robert Mineo and Philip D. Wilson, Jr. "Complications after Total Hip Replacement" *The Journal of Bone and Joint Surgery*, vol. 71-A, No. 4, Apr. 1989 (pp. 528-534).

www.Viasyssupplies.com, "Long Lead Hook-Wire Electrodes, Intra-Operative Monitoring, Products and Accessories, Electrodes & Accessories" Jul. 6, 2007 (2 pages).

\* cited by examiner

SYSTEM AND METHOD FOR LAPAROSCOPIC NERVE DETECTION

BACKGROUND OF THE INVENTION

1. Field of the Invention

The present invention relates in general to the field of laparoscopic surgery, and more particularly to a system and method for detection and mapping of internal nerve tissue.

2. Description of the Related Art

Traditionally, surgery on internal body parts is performed by cutting an incision in the skin to access the internal body parts. Such open surgery entails a number of known risks including infection, inadvertent damage to other organs and structures, scarring, and loss of blood. In an effort to reduce some of these risks and improve patient outcomes surgeons have developed laparoscopic, and more recently robotic, techniques to perform surgery. Robotic surgery is essentially an advanced type of laparoscopic surgery in which the arms that enter the body cavity are robotically controlled instead of manually controlled. During a laparoscopic or robotic surgery, small incisions are made in the skin through which 5-12 millimeter access ports are placed. These ports serve as doorways through which small working instruments and a camera can be placed. The camera creates a magnified view of the internal organs that the surgeon sees on a monitor or console. Such less invasive laparoscopic and robotic surgeries typically have reduced side effects for the patient to allow a more rapid and complete recovery.

One example where laparoscopic and robotic surgery has gained acceptance with positive results is for the accomplishment of a radical prostatectomy. Conventionally, a radical prostatectomy is performed by cutting an incision at the base of the pelvic bone to gain access to the prostate. Once visible, the prostate is cut from the surrounding tissue and removed. Because the area around the prostate is rich in nerves and muscles that support sexual and urinary functions, a radical prostatectomy can cause severe side effects, including sexual dysfunction and incontinence. For example, up to half of conventionally-performed radical prostatectomies result in permanent erectile dysfunction. In contrast, a radical laparoscopic or robotic prostatectomy has the potential for far fewer side effects. In part, laparoscopic and robotic prostatectomies tend to have fewer side effects because the procedure affords the surgeon improved vision and in the case of robotics in particular, more dexterous tools as well. In the case of robotic surgery the improved vision and dexterity of the tools permits a skilled surgeon to better preserve sexual function nerves with as few as ten percent of patients being impotent as a result.

Although laparoscopic and robotic surgery has shown promising potential in reducing erectile dysfunction as a side effect of prostate gland removal, erectile dysfunction does still occur. In some instances, erectile dysfunction after a laparoscopic or robotic prostatectomy cannot be prevented due to Wallerian degeneration of nerves after even a slight injury. However, in some cases erectile dysfunction results from inadvertent damage done to the neurovascular bundle (NVB) that supports erectile function because the NVB is not where the surgeon expects. Direct visualization and appearance of the presumed NVB has not traditionally been a good indicator of preserved erectile nerves. The NVB travels from the base of the prostate where it joins with the bladder, to the apex (the portion where the urethra enters the penis). These nerves travel on opposing sides in a symmetrical fashion on the outside of the prostate capsule on its undersurface at the four and eight o'clock positions. Previous attempts at nerve monitoring during radical prostatectomy used electrical stimulation along the NVB with measurement of the signal in the cavernous bodies via a measurement of intracavernous pressures, i.e., muscle response to electrical stimulation. This method is not time efficient and recent studies have indicated that outcomes are inconsistent with the intraoperative findings.

SUMMARY OF THE INVENTION

Therefore a need has arisen for a rapid and precise system and method which aids in the detection and mapping of nerves during laparoscopic surgery.

In accordance with the present invention, a system and method are provided which substantially reduce the disadvantages and problems associated with previous methods and systems for performing laparoscopic surgery with reduced risk of damage to internal nerves, such as laparoscopic prostate removal with reduced risk of damage to erectile nerves. A probe inserted through the body surface with a catheter and into a body cavity is accessible by a laparoscopic device for placement proximate a nerve. A second probe placed along a presumed pathway of the nerve completes an electrical circuit with the first probe through the nerve so that an electrical signal communicates between the probes. Analysis of the electrical signal supports mapping of the approximate nerve pathway through the body cavity.

More specifically, a handle has first and second catheters, the catheters providing a path for inserting first and second electrode probes through a body and into a body cavity. The electrode probes extend through the catheter and into the body cavity to be accessible for manipulation by a laparoscopic or robotic device. The laparoscopic or robotic device extends the electrode probe into the body cavity for coupling proximate a selected nerve. Through a laparoscopic channel an exploratory probe is placed at various locations along a presumed nerve pathway, the exploratory probe applying a predetermined electrical signal that travels through the nerve to the electrode probe. An analyzer interfaced with the electrode probe provides an indication of the proximity of the exploratory probe to the nerve, such as an audible sound or visually-depicted signal that varies in intensity with the intensity of the electrical signal received at the electrode probe. Placement of the exploratory probe at various points along the presumed nerve pathway allows a mapping of the approximate actual nerve pathway by noting the points at which the electrical signal is relatively strongest. Being able to avoid the approximated nerve pathway while dissecting within the body cavity helps to reduce the risk of nerve damage.

The present invention provides a number of important technical advantages. One example of an important technical advantage is that nerve pathways internal to the body are detectable during laparoscopic and robotic surgery to help the surgeon avoid inadvertent damage to the nerves. Detection of nerve pathways is rapid and precise by variable signals, such as an audible tone or visual signal, that reflect the proximity of a probe to the nerve pathway. Monitoring of nerve pathways is made possible throughout a surgical procedure with readily accessible probes managed with laparoscopic or robotic tools. Probe pairs provide convenient monitoring where nerves serve an area of interest, such as the pair of NVBs that travel from the four and eight o'clock positions under the prostate gland.

Thus, in keeping with the various goals and advantages described, the invention is, briefly, a surgical system for identifying the location of an internal nerve within a body cavity of a body. The system includes at least one electrode probe adapted for inserting into the body cavity through a surface of the body to a position accessible by a laparoscopic device disposed in the body cavity. The at least one electrode probe is positionable by the laparoscopic device within the body cavity and is operable to couple to the body within the body cavity proximate to a preselected nerve. The invention further includes at least one exploratory probe adapted to be disposed in the body cavity and operable to introduce an electrical signal to the body within the body cavity along the presumed pathway of the preselected nerve and distal to the at least one electrode probe to thereby selectively provide an electric signal through the nerve to the at least one electrode probe. The invention further includes, briefly, an analyzer interfaced with the at least one electrode probe, the analyzer being operable to indicate the proximity of the at least one exploratory probe to the preselected nerve based on a measurement of the strength of the electrical signal sensed by the at least one electrode probe and to thereby permit mapping of the location of the preselected nerve.

BRIEF DESCRIPTION OF THE DRAWINGS

The present invention may be better understood, and its numerous objects, features and advantages made apparent to those skilled in the art by referencing the accompanying drawings. The use of the same reference number throughout the several figures designates a like or similar element.

DETAILED DESCRIPTION

Selectively applying electrical current through a nerve within a body cavity allows a surgeon to map the position of the nerve's pathway through the body cavity. By having an approximate map of the nerve pathway, the surgeon is able to dissect regions of the body near the nerve with a reduced risk of damage to the nerve. Thus, for instance, cancerous portions of the body are surgically removed by selecting dissection points as distal to the nerve as is practical. One example of a dissection presented below is the dissection of a prostate gland from within the abdominal cavity using laparoscopic or robotic techniques. Identification of the neurovascular bundle (NVB) that supports erectile function helps to preserve those nerves that support erectile function after removal of the prostate gland. Repeated probing along the presumed pathway of the NVB proximate to the prostate gland maps the approximate location of the NVB, allowing the surgeon to select dissection points that reduce the risk of damage to the NVB. Although a prostate dissection is presented as an exemplary use of the mapping of a nerve pathway through a body cavity, other types of surgeries may benefit from application of the disclosed laparoscopic nerve mapping procedure. In addition, the use of electrode probes supports mapping of nerve pathways that are sometimes found both inside and outside of the body's skin surface.

Figure 1:
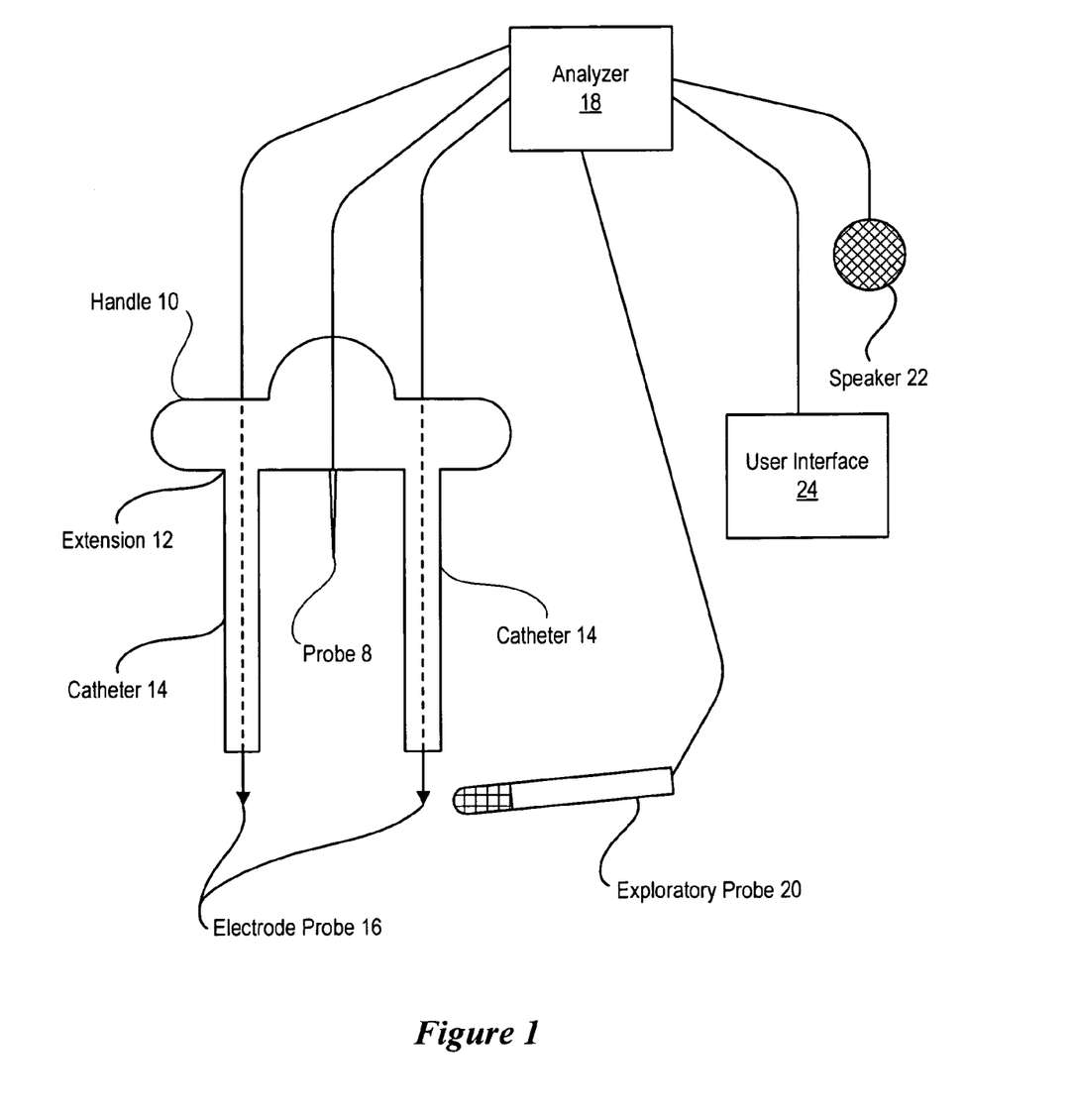
FIG. 1 depicts one embodiment of a system for identifying nerve pathways within a body cavity.

Referring now to FIG. 1, one embodiment of a system for identifying nerve pathways within a body cavity is depicted. A handle 10 has a probe 8 and two extensions 12, each extension having an integrated catheter 14. Handle 10 and catheters 14 provide a pathway for travel of an electrode probe 16 exposed at the end of each catheter 14. Electrode probes 16 are interfaced through a wire or other communication device with an analyzer 18 so that electrical signals, such as voltage and current levels, detected at each electrode probe are communicated to analyzer 18. Probe 8 provides patient grounding when catheters 14 are inserted into the body by interfacing with analyzer 18 through a ground wire. Analyzer 18 interfaces with an exploratory probe 20 and selectively sends a predetermined electrical signal to exploratory probe 20, such as a predetermined current. The electrical signal is passed by exploratory probe 20 to the body of a surgery subject proximate a presumed nerve pathway and received by an electrode probe 16 coupled to the body at a distal point also proximate the presumed nerve pathway. Because nerve tissue conducts an electrical current better than other body tissues, the relative strength of the electrical signal recorded at an electrode probe 16 will increase as exploratory probe 20 is placed closer to the nerve to which the electrode probe 16 is proximately coupled. Thus, by moving exploratory probe 20 along the presumed nerve pathway, analyzer 18 approximately maps the actual nerve pathway based upon the strength of the signal recorded at electrode probe 16 for each position of exploratory probe 20.

The surgical system depicted by FIG. 1 is built from material adapted for use by laparoscopic and robotic devices to support mapping of nerve pathways through a body cavity. For example, handle 10, catheters 16 and electrode probes 16 are built as an integrated unit for one time use and disposal. For instance, handle 10 is formed from non-conductive hard plastic and catheters 14 are integrated in the handle housing and made of Teflon-coated stainless steel. Electrode probes 16 are thin, insulated wires which have a length sufficient to reach the desired area within the body cavity when grabbed by a laparoscopic or robotic device and pulled from the end of catheter 14 to the desired area. As an example of dimensions that suffice for a prostatectomy, the canula length of catheters 14 extending from handle 10 is approximately between 45 mm and 65 mm and the distance between the canula lengths of catheters 14 is approximately 20 mm. Electrode probes 16 are, for example, recording electrodes suitable for manipulation by a laparoscopic robotic arm under direct laparoscopic vision, such as with an extendable length of approximately 50 cm from the end of catheter 14. Analyzer 18 interfaces with a speaker 22, which outputs an auditory signal having an interval and intensity related to the strength of the electrical response detected at electrode probe 16. Thus, for example, a surgeon maps a nerve pathway by listening to the intensity of the auditory response output at speaker 22 and comparing the auditory responses of different positions of exploratory probe 20. Alternatively, a user interface 24 provides visual analysis of the nerve pathway as well as control over the signal provided at exploratory probe 20.

Figure 2:
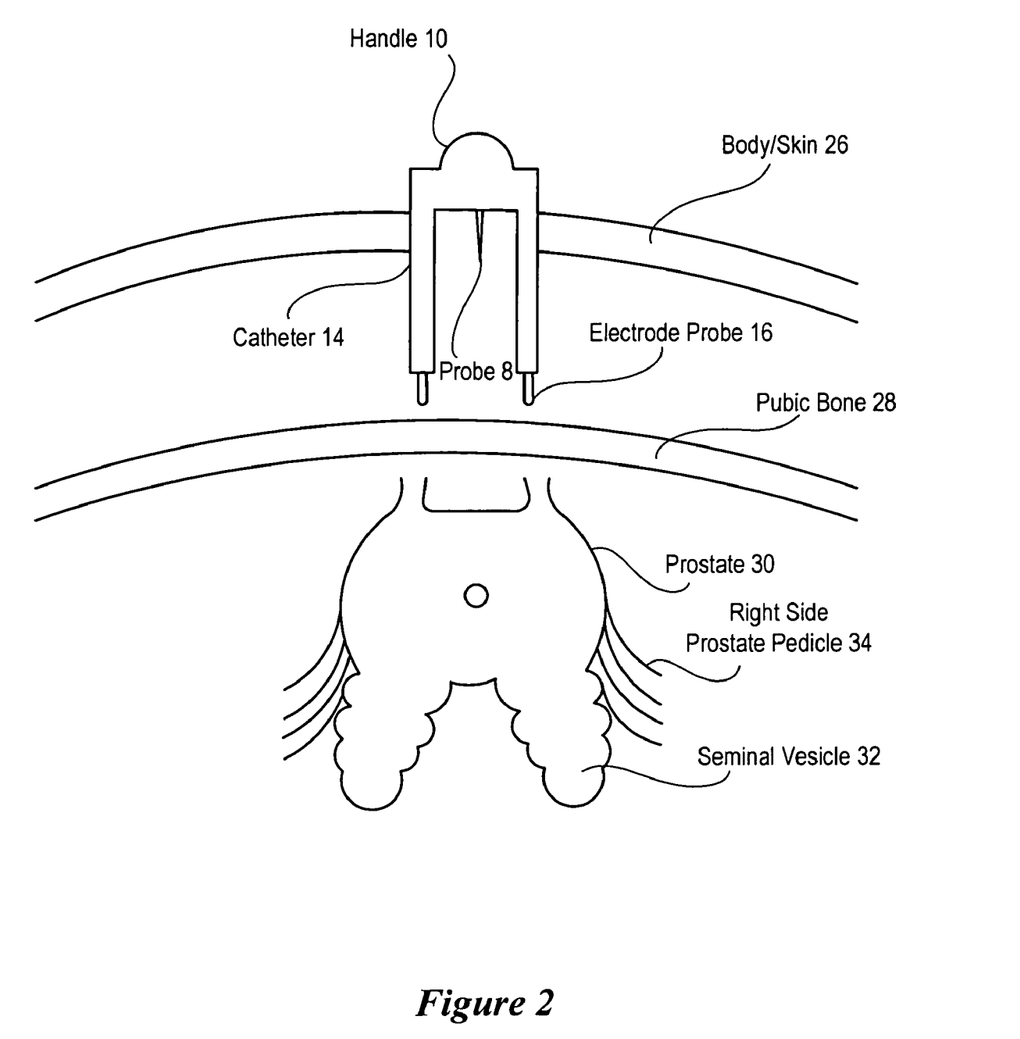
FIG. 2 depicts insertion of a dual electrode probe with a dual catheter through a body surface and into a body cavity.

Referring now to FIG. 2, insertion of a dual electrode probe with a dual catheter through a body surface and into a body cavity is depicted. Handle 10 engages the body skin 26 to insert catheters 14 into the abdominal cavity suprapubically. Catheters 14 provide a pathway through body skin 26 to provide access to electrode probes 16 within an abdominal cavity. The pubic bone 28 sits above the prostate 30 and seminal vesicles 32 within the abdominal cavity. Dissection of prostate 30 requires cutting at the prostate pedicle 34 through which neurovascular bundles (NVBs) travel that support erectile function. During laparoscopic or robotic surgery, laparoscopic devices or robotic devices, such as robotic arms, are inserted into the abdominal cavity to allow dissection of prostate 30.

Figure 3:
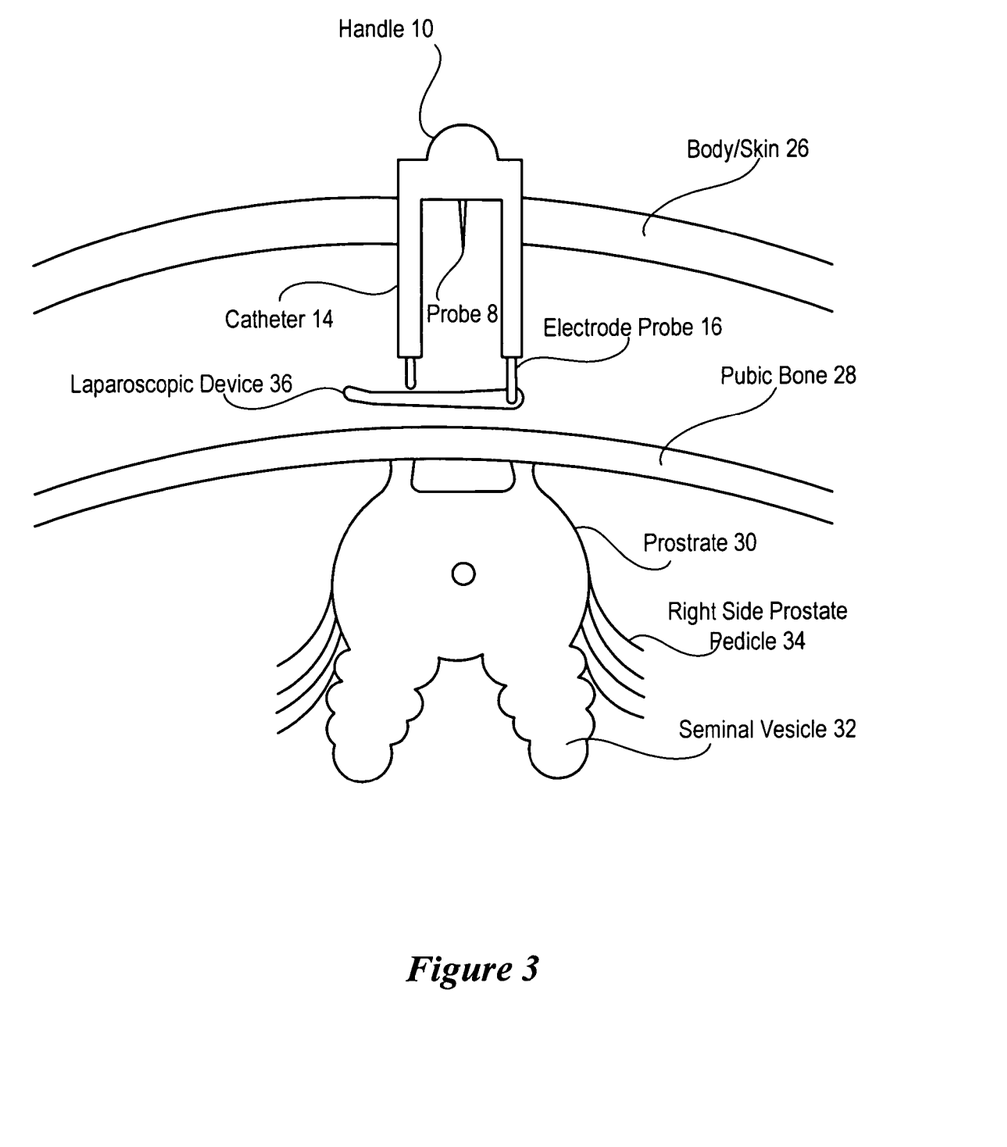
FIG. 3 depicts positioning of an electrode probe with a laparoscopic device to couple to the body within the body cavity proximate a nerve.

Referring now to FIG. 3, positioning of an electrode probe with a laparoscopic device to couple to the body within the body cavity proximate a nerve is depicted. Each catheter 14 allows safe insertion of self-contained recording electrode probe 16 where the probes 16 are visible to laparoscopic vision while simultaneously grounding the body through probe 8. Under direct laparoscopic vision, a laparoscopic device or robotic device 36 grabs electrode probe 16 to move probe 16 to a desired location proximate a nerve of interest. Laparoscopic device 36 advances the probe 16 on the right hand side to a position proximate the NVB on the right hand side of prostate 30 and advances the probe 16 on the left hand side to a position proximate the NVB on the left hand side of prostate 30. Probes 16 temporarily couple to the body so that they remain in position until removed by laparoscopic device 36.

Figure 4:
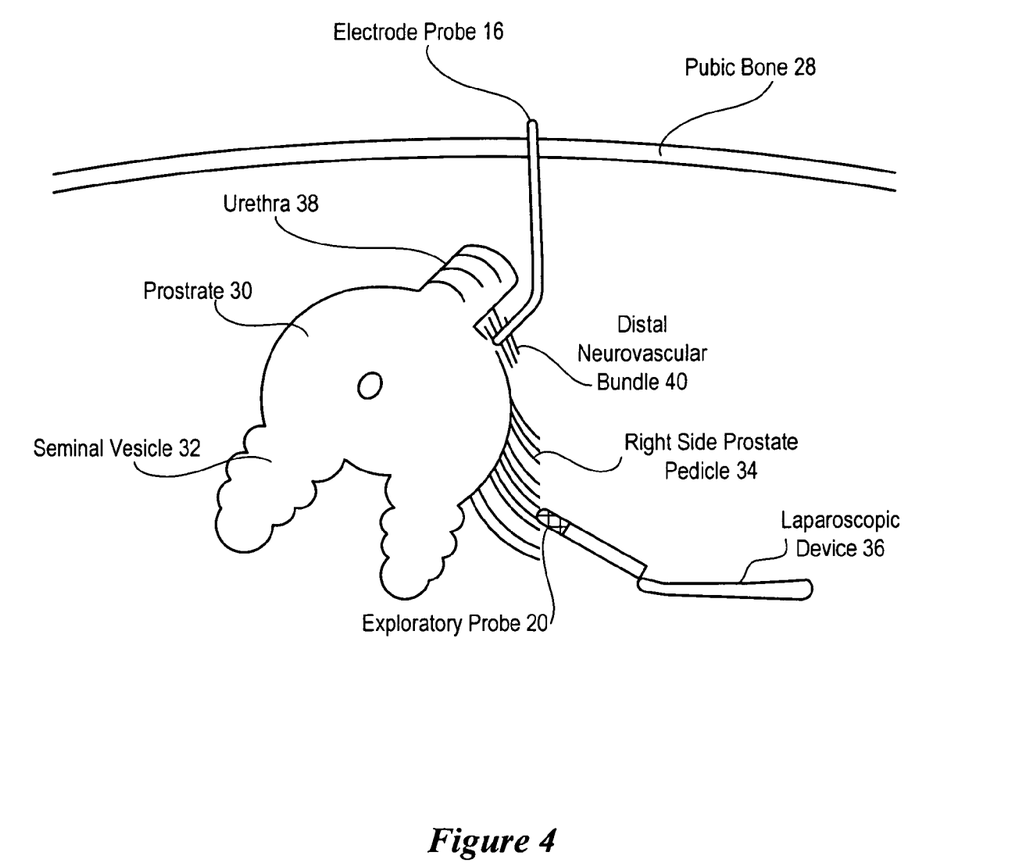
FIG. 4 depicts an exploratory probe providing an electrical current along a presumed pathway of the nerve to map the nerve pathway.

Referring now to FIG. 4, an exploratory probe 20 providing an electrical current along a presumed pathway of the nerve to map the nerve pathway is depicted. Electrode probe 16 attaches at the apex of prostate 30 near where the urethra enters the penis. The position at the apex of prostate 30 is a consistent position for the distal NVB 40 just before it enters into the penis. Electrode probe 16 is of appropriate length to attach at the apex of prostate 30 and is pre-fabricated into handle 10 and catheter 14 to make connection of the recording probe to the body simple and reliable. Once probe 16 is connected to the body at the consistent location of the nerve of interest, electrical stimulation is achieved by delivering a low stimulation current through an exploratory probe 20, which is of known variety, such as a laparoscopic or robotic bipolar instrument. The nerves of interest (e.g. erectile nerves) are stimulated more or less depending on the proximity of the electrified bipolar instrument. Initial searching for the nerve is performed at relatively high stimulus intensities, such as up to about 3.5 milliamp, or even possibly as high as 10 milliamp of current. Searching is performed by placing exploratory probe 20 at several places around the presumed pathway of the nerve and listening for an auditory response from the speaker as well as a visual confirmation on user interface 24 as provided by analyzer 18 that reflects the strength of the electrical signal received at probe 16. Once the nerve's general pathway is mapped, the stimulus intensity provided at exploratory probe 20 is reduced, such as to a level of one-half a milliamp, to map the nerve's location more precisely.

Figure 5:
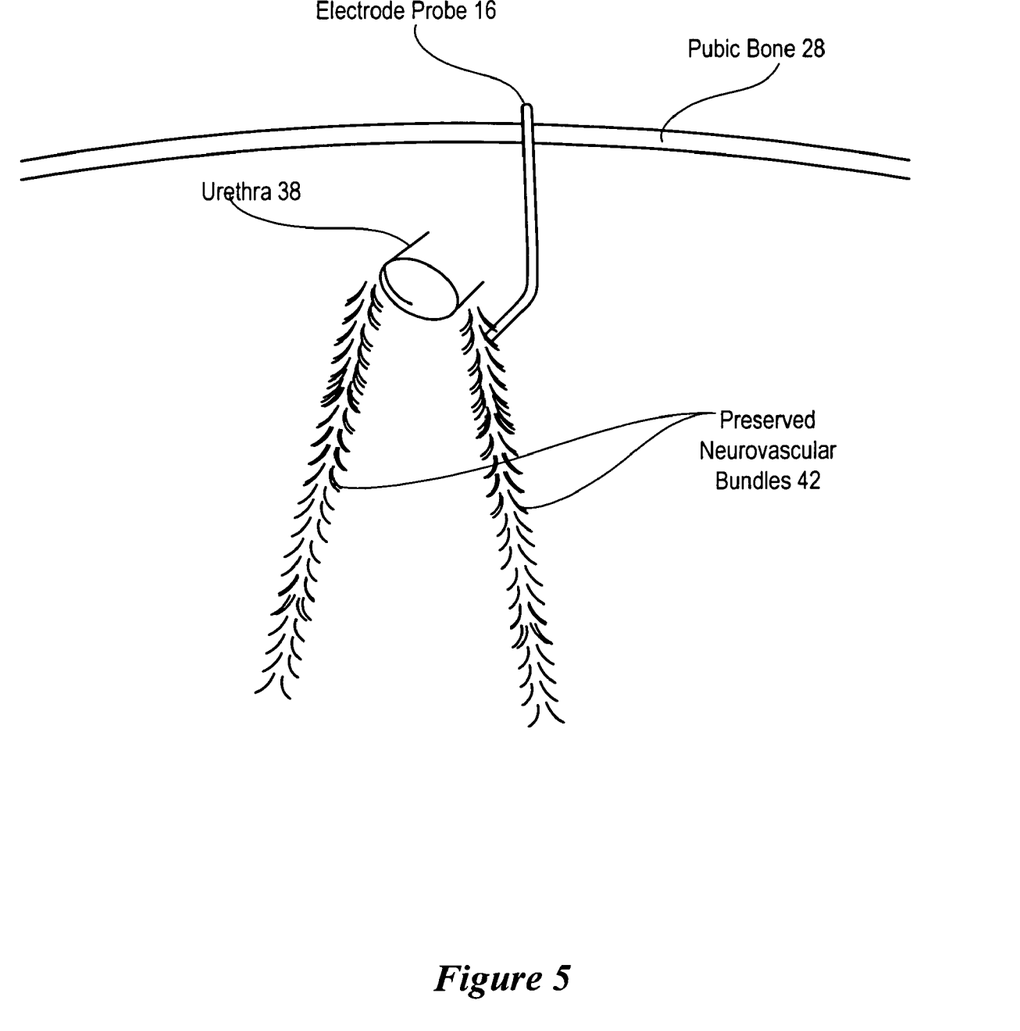
FIG. 5 depicts a postoperative position of the nerve pathway after removal of a prostate gland.

Referring now to FIG. 5, a postoperative position of the nerve pathway after removal of a prostate gland is depicted. Throughout dissection of the prostate, exploratory probe 20 is used to re-map and confirm the position of preserved NVB 42. The objective is to confirm the location of the preselected nerves of interest so that tissue may be selectively preserved or removed depending on the aggressiveness of the cancer. Although the example presents preservation of the nerves in the NVB during a prostatectomy, other types of nerves may be identified and preserved within the abdominal cavity or other body cavities.

Although the present invention has been described in detail, it should be understood that various changes, substitutions and alterations can be made hereto without departing from the spirit and scope of the invention as defined by the appended claims.

What is claimed is:

1. A surgical system for mapping the location of an internal nerve within a body cavity of a body, the system comprising:
   a handle securable to the exterior of the body;
   at least one catheter fixed to the handle, the at least one catheter operable to insert through a body surface to provide access to the body cavity;
   at least one electrode probe adapted to pass through the at least one catheter to a position accessible by a laparoscopic device disposed in the body cavity, the at least one electrode probe operable to be pulled through from the at least one catheter under the influence of the laparoscopic device and independently of any movement of the handle or catheter, to couple the at least one electrode probe to the body within the body cavity proximate to a nerve;
   an exploratory probe separate and distinct from the at least one electrode probe, and which is adapted to be disposed in the body cavity and operable to introduce an electrical signal to the body within the body cavity proximate the nerve and distal the at least one electrode probe; and
   an analyzer interfaced with the at least one electrode probe, the analyzer operable to indicate the proximity of the exploratory probe to the nerve based on the strength of an electrical signal sensed at the at least one electrode probe, to thereby determine the location of the nerve.

2. The surgical system of claim 1 wherein the electrical signal introduced by the exploratory probe comprises a selectively variable current having a range of approximately one-half a milliamp to one milliamp.

3. The surgical system of claim 1 wherein the analyzer comprises an audible signal reflecting the relative strength of the electrical signal sensed at the electrode probe.

4. The surgical system of claim 3 wherein the audible signal reflects relatively closer proximity of the exploratory probe to the nerve for relatively increased electrical signal strength.

5. The surgical system of claim 1 wherein the at least one catheter comprises a first catheter and a second catheter and the at least one electrode probe is a first electrode probe and a second electrode probe, the first electrode probe and the second electrode probe aligned to couple to a first nerve and a second nerve within the body cavity.

6. The surgical system of claim 5 wherein the first nerve and the second nerve are symmetrical and comprise first and second neurovascular bundles proximate a prostate apex.

7. The surgical system of claim 6 wherein the handle comprises a stainless steel portion for patient grounding.

8. A system for detecting nerves disposed in a body, the system comprising:
   a handle securable to the exterior of the body, and having a first extension and a second extension;
   a first electrode probe passing through the first extension and movably operable, under the influence of a laparoscopic device and independently of any movement of the handle, to couple to the body proximate a first nerve; and
   a second electrode probe passing through the second extension and movably operable, under the influence of a laparoscopic device and independently of any movement of the handle, to couple to the body proximate a second nerve;
   wherein the first electrode and the second electrode are further operable to detect electrical signals sent from an exploratory probe, which is separate and distinct from the first electrode probe and the second electrode probe, through the first nerve and the second nerve, respectively.

9. The system of claim 8 further comprising:
a first catheter coupled to the first extension and operable to guide the first electrode probe through a body surface into a body cavity; and
a second catheter coupled to the second extension and operable to guide the second electrode probe through the body surface into the body cavity.

10. The system of claim 9 wherein the handle comprises plastic.

11. The system of claim 8 further comprising an analyzer interfaced with the first electrode probe and the second electrode probe, the analyzer operable to analyze the electrical signals detected at the first electrode probe and the second electrode probe to indicate the proximity of the exploratory probe to the first nerve and the second nerve, respectively, to thereby determine the location of the nerve.

12. A surgical system for mapping the location of an internal nerve within a body cavity of a body, the system comprising:
at least one electrode probe adapted for inserting into the body cavity through a surface of the body to a position accessible by a laparoscopic device disposed in the body cavity, the at least one electrode probe being positionable by the laparoscopic device within the body cavity and operable to couple to the body within the body cavity proximate to a preselected nerve;
at least one exploratory probe separate and distinct from the at least one electrode probe, and which is adapted to be disposed in the body cavity and operable to introduce an electrical signal to the body within the body cavity along the presumed pathway of the preselected nerve and distal to the at least one electrode probe to thereby selectively provide an electric signal to the at least one electrode probe; and
an analyzer interfaced with the at least one electrode probe, the analyzer being operable to indicate the proximity of the at least one exploratory probe to the preselected nerve based on a measurement of the strength of the electrical signal sensed by the at least one electrode probe and to thereby determine the location of the nerve.

13. The surgical system of claim 12, wherein the electrical signal introduced by the exploratory probe comprises a selectively variable current having a range of approximately one-half milliamp to approximately ten milliamps.

14. The surgical system of claim 12, wherein the analyzer comprises an audible signal reflecting the relative strength of the electrical signal sensed at the electrode probe.

15. The surgical system of claim 14 wherein the audible signal reflects relatively closer proximity of the exploratory probe to the nerve for relatively increased electrical signal strength.

16. The surgical system of claim 12, wherein the analyzer comprises a visual signal reflecting the relative strength of the electrical signal sensed at the electrode probe.

17. The surgical system of claim 16 wherein the visual signal reflects relatively closer proximity of the exploratory probe to the nerve for relatively increased electrical signal strength.

18. The surgical system of claim 1 wherein the at least one electrode probe comprises a first electrode probe and a second electrode probe, the first electrode probe being adapted to be couplable near a pre-selected first nerve and the second electrode probe being adapted to be couplable near a pre-selected second nerve to thereby permit a mapping of the second pre-selected nerve immediately subsequent to mapping of the first pre-selected nerve without removal and repositioning of the first electrode probe to necessarily reduce surgical time and risk.

19. The surgical system of claim 12 and further comprising at least one catheter operable to insert through the body surface to enhance access of the at least one electrode probe to the body cavity.

20. The surgical system of claim 19 and further comprising a handle connected to the at least one catheter, wherein the at least one electrode probe is operable independently of any movement of the handle or catheter.

21. A surgical system for mapping the location of an internal nerve within a body cavity of a body, the system comprising:
a handle securable to the exterior of the body;
a catheter fixed to the handle, the catheter operable to insert through a body surface to provide access to the body cavity;
an electrode probe adapted to pass, independently of any movement of the handle or catheter, through the catheter to a position accessible by a laparoscopic device disposed in the body cavity, the electrode probe operable to be pulled through the catheter under the influence of the laparoscopic device to couple to the body within the body cavity proximate to a nerve;
an exploratory probe separate and distinct from the electrode probe, and which is adapted to be disposed in the body cavity and operable to introduce an electrical signal to the body within the body cavity proximate the nerve and distal the electrode probe; and
an analyzer interfaced with the electrode probe, the analyzer operable to indicate the proximity of the exploratory probe to the nerve based on the strength of an electrical signal sensed at the electrode probe, to thereby determine the location of the nerve.

* * * * *